(12) United States Patent
Tess et al.

(10) Patent No.: US 7,086,277 B2
(45) Date of Patent: Aug. 8, 2006

(54) DEVICE HAVING A FLOW CHANNEL CONTAINING A LAYER OF WICKING MATERIAL

(75) Inventors: Mark E. Tess, Merrimack, NH (US);
Scott L. Bailey, Burlington, MA (US);
Shridhara Alva Karinka, Chelmsford, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/784,764

(22) Filed: Feb. 23, 2004

(65) Prior Publication Data

US 2005/0183494 A1 Aug. 25, 2005

(51) Int. Cl.
*G01N 11/00* (2006.01)
*G01N 27/00* (2006.01)

(52) U.S. Cl. ............... 73/53.01; 73/61.41; 204/403.1; 204/403.14; 422/58; 422/82.02

(58) Field of Classification Search .............. 73/53.01, 73/61.41; 204/403.1, 403.14; 422/55, 56, 422/57, 58, 82.01, 82.02, 82.03
See application file for complete search history.

(56) References Cited

U.S. PATENT DOCUMENTS

| 5,141,868 | A |   | 8/1992 | Shanks et al. |         |
|-----------|---|---|--------|---------------|---------|
| 5,385,846 | A | * | 1/1995 | Kuhn et al.   | 205/777.5 |
| 5,437,999 | A |   | 8/1995 | Diebold et al.|         |
| 5,509,410 | A |   | 4/1996 | Hill et al.   |         |
| 5,628,890 | A |   | 5/1997 | Carter et al. |         |
| 5,759,364 | A |   | 6/1998 | Charlton et al.|        |
| 5,964,993 | A |   | 10/1999| Blubaugh, Jr. et al. |  |
| 5,997,817 | A |   | 12/1999| Crismore et al.|        |
| 6,207,000 | B1|   | 3/2001 | Schwobel et al.|        |
| 2004/0067166 | A1 |   | 4/2004 | Karinka et al. | 422/82.03 |
| 2004/0238358 | A1 | * | 12/2004 | Forrow et al. |         |

FOREIGN PATENT DOCUMENTS

WO 2004/108949 12/2004

OTHER PUBLICATIONS

"Pressure—Sensitive Adhesives and Products". Encyclopedia of Polymer Science and Engineering, vol. 13, 1988, John Wiley and Sons; pp. 345-368.
N. J. Forrow et al., "BIOSENSOR". U.S. Appl. No. 10/448,643, filed May 30, 2003.
Copy of The PCT Search Report.

* cited by examiner

*Primary Examiner*—Daniel S. Larkin
(74) *Attorney, Agent, or Firm*—David L. Weinstein

(57) ABSTRACT

A device having a flow channel, wherein a layer of mesh is adhered to a surface forming a wall of a flow channel, but the layer of mesh is of such dimensions that the layer of mesh does not contact those portions of the device where electrochemical reactions occur and electrons flow. In one aspect, the invention provides a sensor, such as, for example, a biosensor, in the form of a strip, the sensor being suitable for electrochemical or optical measurement. The sensor comprises a base layer and a cover layer having a layer of mesh adhered thereto, and the base layer is separated from the cover layer by a spacer layer. The base layer, the cover layer having a layer of mesh adhered thereto, and the spacer layer define a flow channel into which a liquid sample is drawn therein and flows therethrough by means of wicking.

16 Claims, 7 Drawing Sheets

DEVICE HAVING A FLOW CHANNEL CONTAINING A LAYER OF WICKING MATERIAL

FIELD OF THE INVENTION

This invention relates to a device for improving the flow of a fluid in a channel where the flow results from wicking. More particularly, the invention relates to a sensor for determining the concentration of an analyte in a liquid sample where the liquid sample is transported to a reaction site of the sensor by a layer of mesh.

DISCUSSION OF THE ART

Controlling the flow of fluid in a channel where the flow results from wicking is important in microfluidic and microanalytical systems. The volume of fluid in an area where a chemical reaction is to be carried out often is required to be controlled to ensure precise control of the reaction or precise quantification of the analyte of interest or both. When the dimensions of the channel are so small as to reduce the volume of fluid that can be transported in a given period of time, the rapid uptake of viscous fluids, e.g., whole blood, becomes a problem.

The prior art discloses numerous electrochemical and optical test strips for measuring the concentration of an analyte in a test sample. In particular, the art discloses disposable test strips for the measurement of glucose level in whole blood that deal primarily with the reaction layer used to generate an analytical response, the mode of measurement, and the algorithms used in the measurement.

Introduction of a liquid sample to these test strips can be achieved in several ways. A simple approach is to place a sample of liquid directly onto the reaction site. A second approach is to define a cavity having dimensions small enough to allow the liquid sample to be taken up by capillary attraction. An alternative to the use of capillary attraction is to place a layer of mesh in the sample path to aid in transporting the sample by wicking action to fill the reaction site.

U.S. Pat. No. 5,509,410 discloses a strip comprising an elongated support (preferably flat) adapted for releasable attachment to readout circuitry; a first conductor and a second conductor each extending along the support and comprising means for connection to the circuitry. An active electrode, positioned to contact a liquid mixture and the first conductor, comprises a deposit of enzyme capable of catalyzing a reaction involving a compound and (preferably) an electron mediator, capable of transferring electrons between the enzyme-catalyzed reaction and the first conductor. A reference electrode is positioned to contact the mixture and the second conductor.

U.S. Pat. No. 5,141,868 discloses a specifically-reactive sample-collecting and testing device having a cavity or cavities, the dimensions of which are small enough to enable a liquid sample to be drawn into the cavity or cavities by capillary attraction. The cavity includes an electrode arrangement for measuring one or more electrical characteristics of the sample. A surface of a wall of the cavity optionally bears a coating of a material that is appropriate for the test to be carried out in the device. In the device, the sample flows by capillary attraction into a biosensor to a point defined by the interface of the cover layer and air.

U.S. Pat. Nos. 5,759,364; 5,437,999; 5,997,817; and 6,207,000 describe the use of flow channels that employ capillary attraction for transporting biological samples in electrochemical sensors.

U.S. Pat. No. 5,628,890 discloses an electrode strip for use in an electrochemical sensor for measuring a compound in a sample. The strip includes an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the support, the covering layer having a sample application aperture spaced from the electrodes and the reference electrode spaced from the working electrode at a position remote from and on the opposite side of the working electrode from the aperture.

Applying a layer of mesh is a time-consuming step, and a sensor employing a layer of mesh may require a larger sample than does a sensor not employing a layer of mesh, primarily because a flow channel having greater dimensions may be required to insert a layer of mesh. Removal of the layer of mesh would result in saving time in production, reducing cost of the sensor, and reducing the volume of sample required. In additional, the layer of mesh blocks a portion of the sample from reaching the electrodes, thereby resulting in a lower than desired signal.

The devices in the art described above either require large volumes of sample on account of the construction of the reaction site in mesh-containing sensors or lack adequate uptake of sample on account of extremely small dimensions in a sensor utilizing flow in a capillary channel. Moreover, a layer of mesh applied over the electrodes modifies the performance of the sensor, e.g., increases solution resistance, occludes the surface of the electrode(s), retards diffusion of the analyte to the surface(s) of the electrode(s), etc.

It would be desired to develop a device that combines the advantages of lower volume of sample of the capillary cell format, e.g., reduced dimensions, and the enhanced flow characteristics brought about by a mesh-containing sensor, e.g., wicking.

SUMMARY OF THE INVENTION

The present invention provides a device having a flow channel, wherein a layer of mesh is adhered to a surface forming a wall of a flow channel, but the layer of mesh is of such dimensions that the layer of mesh does not contact those portions of the device where electrochemical reactions occur and electrons flow.

In one aspect, the invention provides a sensor, such as, for example, a biosensor, in the form of a strip, the sensor being suitable for electrochemical measurement. The sensor comprises a base layer and a cover layer, and the base layer is separated from the cover layer by a spacer layer. The base layer further includes an electrode arrangement on one major surface thereof. The cover layer further includes a layer of mesh overlying the major surface that faces the base layer. The base layer, cover layer bearing a layer of mesh, and spacer layer define a flow channel into which a liquid sample is drawn and through which a liquid sample flows by means of wicking.

In a preferred embodiment, the sensor is in the form of a strip and comprises:

(a) a base layer having a first major surface and a second major surface;

(b) a cover layer having a first major surface and a second major surface, the first major surface of the cover layer facing the first major surface of the base layer, the first major surface of the cover layer having a layer of mesh adhered thereto;

(c) a spacer layer interposed between the first major surface of the cover layer, which bears a layer of mesh, and the first major surface of the base layer to separate the cover layer from the base layer;

(d) a flow channel having walls formed by the first major surface of the cover layer, the first major surface of the base layer, and surfaces of the spacer layer, the flow channel having a reaction site, the layer of mesh not contacting the reaction site;

(e) a sample application zone, where the liquid sample is introduced into the flow channel; and (f) at least one opening communicating with the flow channel to allow gas to be vented from the flow channel.

In the preferred embodiment, the reaction site includes an electrode arrangement comprising at least a working electrode and a reference electrode in the flow channel. In conjunction with the electrode arrangement, at least one reagent for a specified assay can be located at or transported to the reaction site.

In a preferred embodiment, the spacer layer defines the sidewalls of the flow channel, while the cover layer forms the top wall of the flow channel and the base layer forms the bottom wall of the flow channel. Air can be vented from the flow channel via at least one opening formed in the spacer layer, in the cover layer, or in the base layer, the at least one opening communicating with the flow channel.

In a preferred embodiment, the flow channel is closed at the distal end and has no openings in the sidewalls. In this embodiment, the sensor can be vented through the cover layer by at least one, and preferably a plurality of, openings formed therein. The use of a plurality of openings in the cover layer eliminates the problem that results from the use of a single opening that is improperly positioned with respect to the flow channel, with the result that the opening does not connect the flow channel with the external environment. If two or more openings are employed, and if these openings are separated from one another, there is a higher probability that at least one of the openings will serve to vent air from the flow channel. The openings are preferably placed sufficiently close to each other so that no matter how the cover layer is placed over the flow channel, at least one opening, and preferably more than one opening, is positioned over the flow channel to allow venting. At the same time, the openings are preferably separated by sufficient distance so that the mechanical strength of the cover layer is not diminished.

In one embodiment, the invention provides enhancement of the flow of the sample to a reaction site. The mesh that is applied to the cover layer provides a surface to aid the flow of the sample by breaking the surface tension of the sample. However, the layer of mesh does not contact the electrodes positioned at the reaction site.

In another embodiment, the invention allows the reagents to be incorporated into the mesh that is applied to the cover layer of the sensor. The sample dissolves the reagents, and the signal indicative of the concentration of the analyte is measured at the working electrode.

In another embodiment, the invention allows reagents to be deposited on the cover layer in a pattern that will allow the reagents to dissolve in the sample and migrate to the surface of the electrode. The insoluble component(s) of the pattern provides a rough surface over which the sample flows.

DETAILED DESCRIPTION

As used herein, the expression "capillary attraction" means the force that results from greater adhesion of a liquid to a solid surface than internal cohesion of the liquid itself and causes the liquid to flow along a surface, as water is in a clean glass tube.

The expression "reaction site" means that portion of the sensor that contains materials related to the reaction that must take place in order to carry out an assay. The reaction site for an electrochemical sensor includes an arrangement comprising at least a reference electrode and a working electrode. The reaction site of a photometric sensor includes an arrangement comprising an area at which light is transmitted into the flow channel, whereby a change in a property of the light so transmitted is detected. If the sensor includes an optional reagent, the reagent interacts with the sample and assists in the assay by undergoing a change related to the test, whereby a measurement based on a reaction involving the reagent is carried out in conjunction with the electrode arrangement or the photometric arrangement, whichever arrangement is employed.

The expression "wicking" refers to the flow of the sample to the reaction site by means of the mesh. The layer of mesh aids the transfer of sample from the sample application zone to the reaction site. The layer of mesh can be a woven material or a non-woven material or can be applied to the surface of a support by any deposition technique. The layer of mesh helps to draw the sample to the reaction site by reducing the surface tension of the sample, thereby allowing the sample to spread evenly over the reaction site, including the electrodes. As stated previously, the layer of mesh is positioned so as not to contact the electrodes in the electrode arrangement of the sensor.

The term "sample application zone" means the location on the sensor where the sample is applied. The sample application zone is in fluidic communication with the reaction site.

The expression "trigger electrode" means an electrode that detects a fluidic junction and indicates that sufficient quantity of sample has reached the reaction site in order to begin the assay. It is preferred that the trigger electrode be positioned downstream of the working and reference electrodes. When the sample contacts the trigger electrode, an electrical signal is generated to indicate that the volume of sample in the reaction chamber is sufficient for the assay to begin.

Figure 1:
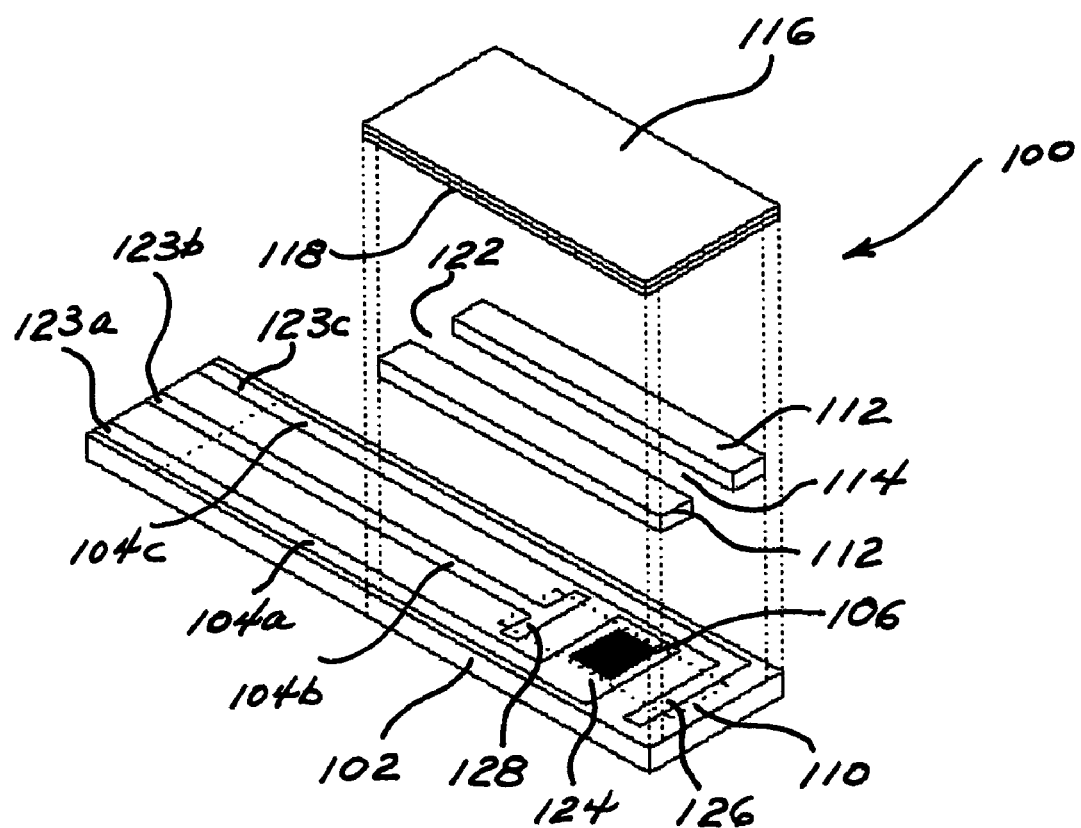
FIG. 1 is an exploded perspective view of one embodiment of the sensor of this invention. The sensor is in the form of a strip.
Figure 2:
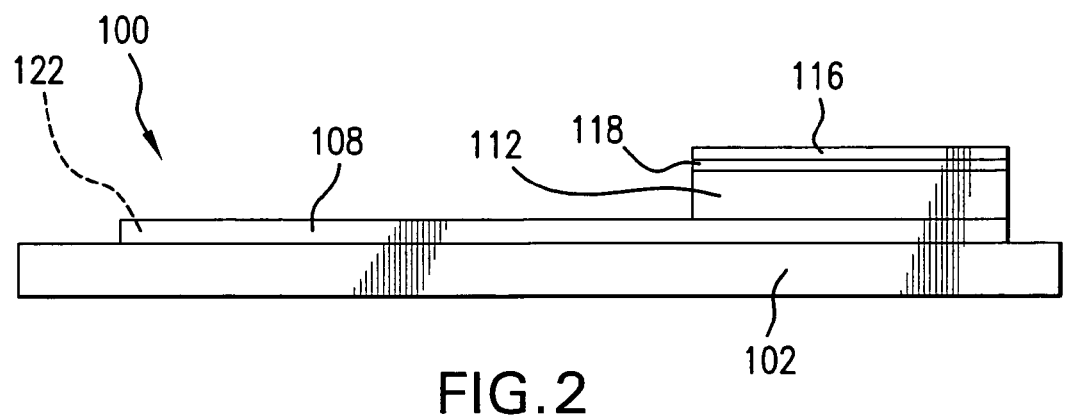
FIG. 2 is a side view in elevation of one side of the sensor shown in FIG. 1.
Figure 3:
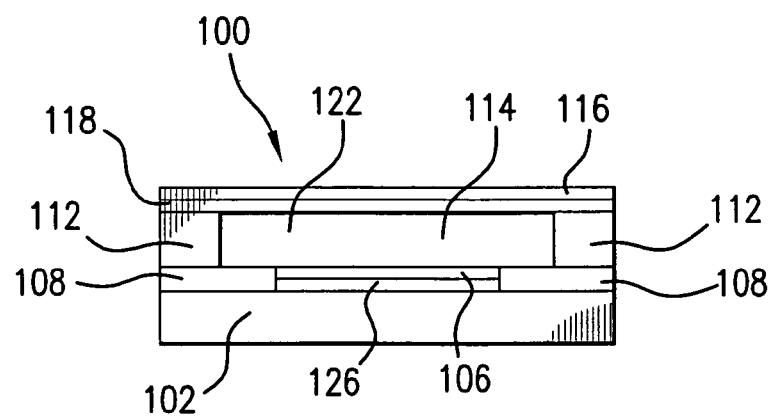
FIG. 3 is a side view in elevation of one end of the sensor shown in FIG. 1.
Figure 4:
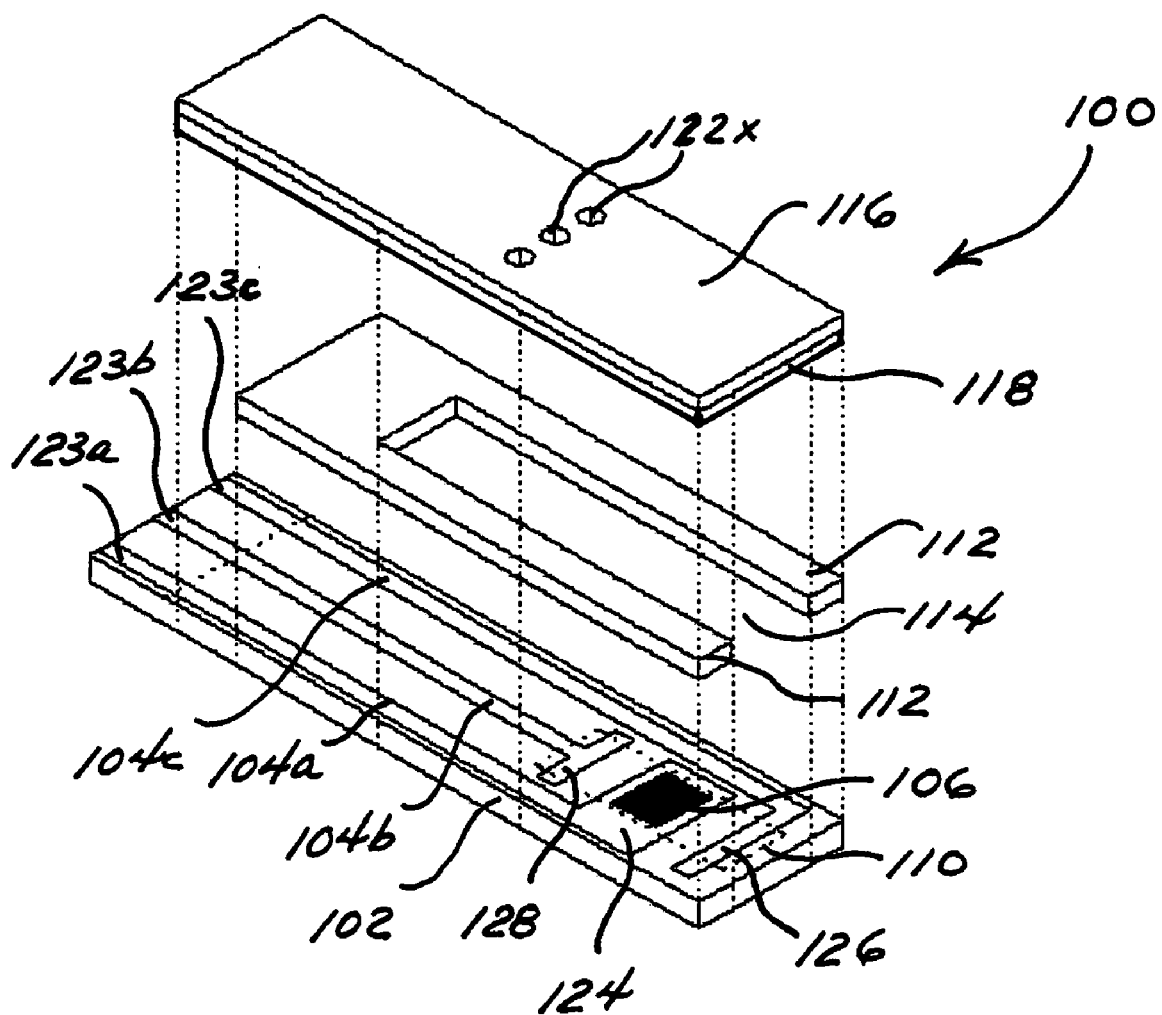
FIG. 4 is an exploded perspective view of another embodiment of the sensor strip of this invention. The sensor is in the form of a strip.
Figure 5:
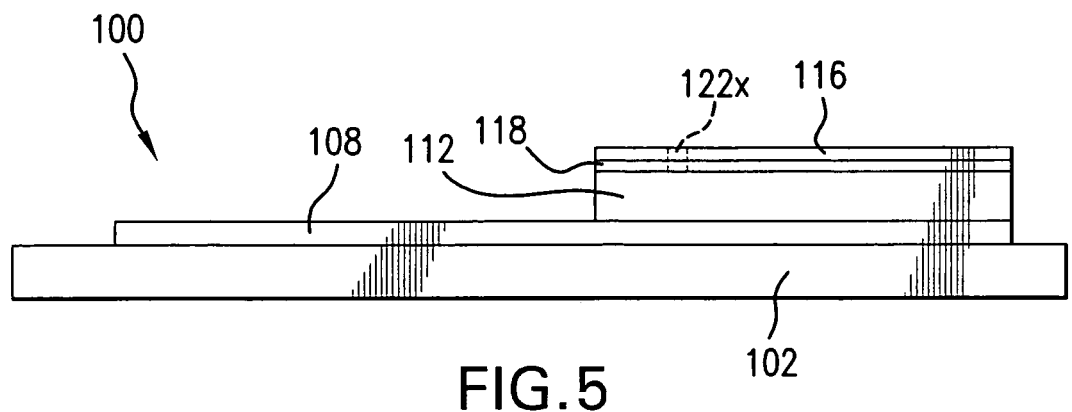
FIG. 5 is a side view in elevation of one side of the sensor shown in FIG. 4.
Figure 6:
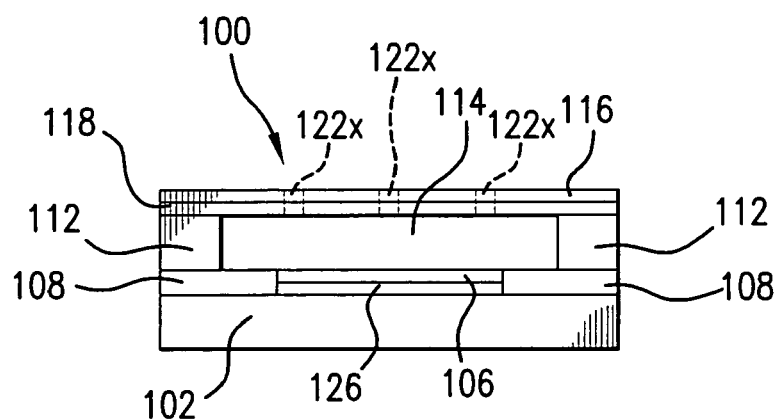
FIG. 6 is a side view in elevation of one end of the sensor strip shown in FIG. 4.

FIGS. 1, 2, and 3 illustrate one embodiment of a sensor in accordance with this invention. FIGS. 4, 5, and 6 illustrate another embodiment of a sensor in accordance with this invention. In order to simplify the discussion of these embodiments, those parts having the same function in each embodiment will have the same reference numeral. The embodiments differ primarily in the location of the opening for the air vent. Those parts in FIGS. 4, 5, and 6 that are substantially different from those parts in FIGS. 1, 2 and 3 will be distinguished by the suffix "x". Accordingly, in FIGS. 4, 5, and 6, the reference numerals for the openings for the vents will be followed by the suffix "x".

Referring now to FIGS. 1, 2, 3, 4, 5, and 6, a sensor 100, in the form of a strip, comprises a base layer 102, conductive tracks 104*a*, 104*b*, and 104*c* for electrochemical use, a reaction site 106, a layer of electrically insulating material 108 to delineate a specified sensor area 110, a spacer layer 112 to specify the width and depth of a flow channel 114, and a cover layer 116 to enclose the flow channel 114.

The cover layer 116 includes a layer of mesh 118 adhered to one major surface thereof. At least one opening is formed in the sensor strip 100 in communication with the flow channel 114 to bleed air to reduce the pressure that resists uptake of the sample. This pressure inhibits the sample from traversing the flow channel 114. In FIGS. 1, 2, and 3, the at least one opening is designated by the reference numeral 122. In FIGS. 4, 5, and 6, the at least one opening is designated by the reference numeral 122*x*.

The base layer 102 is preferably made of an inert polymeric material. Representative materials that can be used to form the base layer 102 include, but are not limited to, poly(vinyl chloride), polycarbonate, and polyester. The dimensions of the base layer 102 are not critical, but a typical base layer 102 has a length of from about 20 mm to about 50 mm, a width of from about 3 mm to about 10 mm, and a thickness of from about 0.3 mm to about 1 mm.

The conductive tracks 104*a*, 104*b*, and 104*c* are made of an electrically conductive material. Representative materials that can be used to form the electrically conductive tracks 104*a*, 104*b*, and 104*c* include, but are not limited to, carbon, platinum, palladium, gold, and a mixture of silver and silver chloride. The tracks 104*a*, 104*b*, and 104*c* determine the positions of electrical contacts 123*a*, 123*b*, and 123*c*, respectively, and the electrodes, which will be described later. The third track can be omitted in the absence of a third electrode. The electrical contacts are insertable into an appropriate measurement device (not shown). A measurement device suitable for use with the sensor of this invention is a glucose monitor having the trademark "PRECISION XTRA", commercially available from MediSense.

The reaction site 106 comprises an arrangement of electrodes, and, optionally, one or more layers of reagents. The electrode arrangement of the sensor preferably includes either two or three electrodes. In a two-electrode system (not shown), a working electrode and dual-purpose reference/counter electrode define the electrode arrangement. A third electrode (trigger electrode) can be optionally added to indicate that the reaction site 106 is filled. The trigger electrode prevents the assay from beginning until an adequate quantity of sample has filled the reaction site 106. A two-electrode system is described more completely in U.S. Pat. No. 5,509,410, incorporated herein by reference. The reference electrode can be positioned so as to act as a trigger electrode to initiate the assay sequence in the absence of the third electrode.

In a three-electrode system, which is illustrated in FIGS. 1, 2, 3, and 4, a working electrode 124, a reference electrode 126, and a counter electrode 128 define the electrode arrangement. The function of the working electrode 124 is to monitor the reaction that takes place in the reaction site 106, e.g., the reaction of glucose with glucose oxidase or glucose dehydrogenase. The function of the reference electrode 126 is to maintain a desired potential at the working electrode. The function of the counter electrode 128 is to provide the necessary flow of current at the working electrode 124. In this system, the counter electrode 128 can have the secondary function of a trigger electrode, that is, the counter electrode 128 prevents the assay from beginning until an adequate quantity of sample has filled the reaction site 106.

The electrochemical reaction that takes place at the working electrode 124 is the reaction that is required to be monitored and controlled, e.g., the reaction of glucose with glucose oxidase or with glucose dehydrogenase. The functions of the reference electrode 126 and the counter electrode 128 are to ensure that the working electrode 124 actually experiences the desired conditions, i.e. the correct potential. The potential difference between the working electrode 124 and the reference electrode 126 is assumed to be the same as the desired potential at the working electrode 124. In an ideal reference electrode, no current passes through the reference electrode, and the reference electrode maintains a steady potential; in the case of a dual-purpose reference/counter electrode, current does pass through the dual-purpose reference/counter electrode, and thus, the dual-purpose reference/counter electrode does not maintain a steady potential. At low currents, the potential shift is small enough such that the response at the working electrode is not significantly affected. The dual-purpose reference/counter electrode still carries out its counter electrode function; however, in the case of the dual-purpose reference/counter electrode, the potential that is applied between the dual-purpose reference/counter electrode and the working electrode cannot be altered to compensate for changes in potential at the working electrode.

The electrodes 124, 126, and 128 are made of an electrically conductive or semiconductive material. Representative materials that can be used to form the electrodes 124, 126, and 128 include, but are not limited to, carbon, platinum, palladium, and gold. The reference electrode 126 can optionally contain a layer comprising a mixture of silver and silver chloride. The dimensions of the electrodes 124, 126, and 128 are not critical, but a typical working electrode has an area of from about 0.5 mm$^2$ to about 5 mm$^2$, a typical reference electrode has an area of from about 0.2 mm$^2$ to about 2 mm$^2$, and a typical counter electrode has an area of from about 0.2 mm$^2$ to about 2 mm$^2$.

The working electrode 124 comprises a layer of conductive material containing a working area. The working area can include an ink (referred to a working ink), which is deposited on the layer of conductive material of the working area. The working ink comprises a reagent system that is sensitive to the analyte of interest.

In a preferred embodiment, the working area contains a working ink that includes a reagent suitable for the subject test. The reagent may include a mixture of an enzyme (e.g., glucose dehydrogenase or glucose oxidase for a glucose assay), an oxidation-reduction mediator (such as an organic compound, e.g., a phenanthroline quinone, an organometallic compound, e.g., ferrocene or a ferrocene derivative, a coordination complex, e.g., ferricyanide), and, optionally, a filler material (e.g., a conductive filler material, such as carbon, or a non-conductive filler material, such as silica). Alternatively, instead of an enzyme, the working area can contain a substrate that is catalytically reactive with an enzyme to be measured. The working ink can be applied to the electrode 124, and, optionally, electrode 126 or electrode 128, or both, as a discrete area of fixed length. The working ink can be applied by means of screen-printing. The working ink can further include a polysaccharide (e.g., a guar gum, an alginate, cellulose or a cellulosic derivative, e.g., hydroxyethyl cellulose), a hydrolyzed gelatin, an enzyme stabilizer (e.g., glutamate or trehalose), a film-forming polymer (e.g., a polyvinyl alcohol), a conductive filler (e.g., carbon) or non-conductive filler (e.g., silica), a defoaming agent, a buffer, or a combination of the foregoing.

The electrodes cannot be spaced so far apart that the working electrode 124, the reference electrode 126, and the counter electrode 128 (or the dual-purpose reference/counter electrode and the working electrode in an alternative embodiment) cannot be covered by the sample. It is preferred that the length of the path to be traversed by the sample (i.e., the sample path) be kept as short as possible in order to minimize the volume of sample required. The maximum length of the sample path can be as great as the length of the sensor. However, the corresponding increase in resistance of the sample limits the length of the sample path to a distance that allows the necessary response current to be generated. The resistance of the sample is also influenced by the magnitude of the shortest distance from an edge of the area of the reference electrode 126 to an edge of the working area of the working electrode 124 (or by the magnitude of the shortest distance from an edge of the dual-purpose reference/counter electrode to an edge of the working area of the working electrode in an alternative embodiment). Reducing the distance between the reference electrode 126 and the working electrode 124 (or the dual-purpose reference/counter electrode from the working electrode in an alternative embodiment) decreases the resistance of the sample. Positioning the electrodes in a spaced-apart manner has the advantage of preventing completion of a circuit (and thus preventing detection of a response current) before the working electrode has been completely covered by sample.

The elongated portions of the conductive tracks 104a, 104b, and 104c can optionally be overlaid with a track of conductive material, preferably made of a mixture comprising silver particles, preferably in the form of a powder, and silver chloride particles, preferably in the form of a powder. This optional overlying track results in lower resistance, and consequently, higher conductivity. Optionally, a layer of electrically insulating material 108 further overlies the tracks 104a, 104b, and 104c. The layer of electrically insulating material 108 does not cover the positions of the reference electrode 126, the working electrode 124, the counter electrode 128, and the electrical contacts 123a, 123b, and 123c. In the embodiment employing the dual-purpose reference/counter electrode (in an alternative embodiment), the layer of electrically insulating material does not cover the positions of the dual-purpose reference/counter electrode, the working electrode, any third electrode, and the electrical contacts. This layer of electrically insulating material 108 serves to prevent short circuits. If this layer of electrically insulating material is hydrophobic, it can cause the sample to be restricted to the exposed electrodes. A preferred electrically insulating material is commercially available as "POLYPLAST" (Sericol Ltd., Broadstairs, Kent, UK). In FIGS. 1 and 4, the layer of electrically insulating material is not numbered, but it comprises a thin layer of material overlying the base layer 102, except in the positions of the reference electrode 126, the working electrode 124, the counter electrode 128, and the electrical contacts 123a, 123b, and 123c. Dashed lines on the base layer indicate the boundaries of the layer of electrically insulating material.

The reaction site 106 is not limited to reaction sites appropriate to electrochemical sensors. In a photometric sensor (not shown), the reaction site can comprise a reagent system that changes its optical properties (e.g., absorbance, reflectance) as a function of the presence of or the amount of an analyte. A photometric sensor is similar to the sensor shown in FIGS. 1, 2, 3, and 4, with the exception that the electrodes and tracks are removed, and, at the reaction site, at least a portion of the flow channel comprises a light transmissive material so that a source of light can transmit light through the light transmissive material to provide a signal related to the presence or the amount of an analyte in the sample, e.g., absorbance or reflectance. This optical signal can be detected and measured. In conjunction with the light transmissive material, at least one reagent for a specified assay can be located at or transported to the reaction site. In still another type of sensor (not shown), the reaction site can comprise an ion-selective electrode.

The spacer layer 112 comprises a material of substantially uniform thickness that can bond to the major surface of the base layer 102 and to the major surface of the cover layer 116 that face each other. The spacer layer 112 can comprise a backing having adhesive material coated on both major surfaces thereof. Examples of backings and adhesives suitable for forming the spacer layer 112 can be found in *Encyclopedia of Polymer Science and Engineering* Volume 13, John Wiley & Sons (1988), pages 345–368, incorporated herein by reference. Alternatively, the spacer layer 112 can be formed by printing an adhesive. Adhesives that are suitable for preparing the spacer layer 112 should be sufficiently resistant to external pressure so that the depth of the spacer layer 112 is maintained upon exposure of the sensor 100 to external stress.

The spacer layer 112 can be prepared in any of several ways. In one embodiment, the spacer layer 112 can be prepared from a double-sided adhesive tape, i.e., a backing layer having a layer of adhesive on both major surfaces thereof. In another embodiment, the spacer layer 112 can be formed from an adhesive that is coated onto the base layer 102 from an aqueous carrier or from an organic carrier. In still another embodiment, the spacer layer 112 can be formed from a radiation curable adhesive, preferably ultra-violet radiation curable adhesive, the adhesive being capable of being coated onto the base layer 102. In still another embodiment, the cover layer bearing a layer of mesh can be laminated to the base layer 102 by means of an inert spacer layer. The dimensions of the spacer layer 112 are not critical, but the spacer layer 112 typically has a length ranging from about 3 mm to about 30 mm and a thickness ranging from about 25 µm to about 200 µm. Surfaces of the spacer layer 112 form the sidewalls of the flow channel 114. A typical width of a flow channel 114 ranges from about 2 mm to about 5 mm.

The spacer layer 112 must be adhered to both the base layer 102 and the cover layer 116 to maintain the sensor 100 as an integrated unit. It is preferred that the spacer layer 112 be bonded to the cover layer 116 and the base layer 102 by means of adhesive. Preferred embodiments of the spacer layer 112 include a backing having a layer of adhesive on both major surfaces thereof. The adhesive can be a water-borne adhesive, a solvent-borne adhesive, or a radiation-curable adhesive, preferably an ultra-violet radiation curable adhesive (hereinafter "UV-curable adhesive"). Water-borne adhesives, solvent-borne adhesives, and UV-curable adhesives are preferably applied by screen-printing so that a required design of the spacer layer 112 is printed on the base layer 102. The required design is preferably prepared from a UV-curable adhesive, because the thickness of the spacer layer that will result from curing the uncured layer of UV-curable adhesive corresponds closely to the thickness of the uncured layer of UV-curable adhesive, thereby ensuring the manufacture of a flow channel 114 having a precisely defined depth.

Commercially available products comprising backings having layers of adhesive on both major surfaces thereof include materials such as TESA 4972 (TESA Tape, Inc., Charlotte, N.C.). Such products are preferably precut before being applied to the base layer 102. U.S. Pat. No. 6,207,000 discloses a process wherein (1) a carrier layer is prepared, (2) a spacer layer is laminated onto the carrier layer, (3) a contour is punched, cut, or stamped through the spacer layer laminated onto the carrier layer which determines the shape of a capillary-active zone, (4) those parts of the spacer layer which are not required to form the capillary-active zone are removed from the carrier layer, and (5) a cover layer is applied to the spacer layer to result in the capillary-active zone. The spacer layer is a double-sided adhesive tape.

Representative examples of water-borne adhesives suitable for use in this invention include materials such as acrylic-based KiwoPrint D-series adhesives (Kiwo, Inc., Seabrook, Tex.). One benefit of water-borne adhesives is that the humidity of the printing environment can be maintained at a desired level to avoid premature drying of the adhesive. One disadvantage of water-borne adhesives is that the depth of the flow channel 114 is reduced significantly when the aqueous carrier evaporates. In addition, water-borne adhesives may not have sufficient mechanical strength to prevent deformation when subjected to externally applied pressure.

Representative examples of solvent-borne adhesives suitable for use in this invention include materials such as acrylic-based KiwoPrint L-series and TC-series adhesives (Kiwo, Inc., Seabrook, Tex.). Solvent-borne adhesives are more difficult to use than are water-borne adhesives, because evaporation of solvent is more facile than water. In addition, the depth of the flow channel 114 decreases significantly following removal of solvent.

Representative examples of UV-curable adhesives suitable for use in this invention include materials such as Kiwo UV3295VP (Kiwo, Inc., Seabrook, Tex.), which comprises acrylic acid, benzophenone, isobornyl acrylate, isobornyl methacrylate, proprietary photoinitiator, and proprietary acrylic oligimer and polyesters. Advantages of UV-curable adhesives include resistance to drying under ambient conditions (i.e., external ultraviolet radiation is required to initiate polymerization) and the ability to maintain the thickness of layer immediately following printing throughout the curing process. As mentioned previously, the depth of the flow channel 114 derived from thickness of water-borne and solvent-borne adhesives decreases upon curing (reduction in the depth of the flow channel 114 ranges from about 40% to about 70%). The viscosity of the UV-curable adhesive can be modified from the original formulation by the inclusion of fumed silica (Cab-O-Sil M5, Cabot Corporation, Boston, Mass.). The addition of fumed silica (preferably up to 3% by weight) allows modification of viscosity without adversely affecting the bonding characteristics of the cured adhesive. The increased viscosity of the ink improves the definition of the walls of the flow channel by reducing the ability of the ink to spread between the time it is printed and the time it is cured. The thickness of the spacer layer 112 can be controlled by selecting appropriate mesh counts and thread thickness of the screen used for printing these adhesives. Alternatively, the adhesive can be screen printed by means of a stencil screen of desired thickness.

Registration tolerances of a spacer layer 112 applied by a method of printing are well suited for rapid manufacturing of a sensor having the form of a strip. In particular, the material for forming the spacer layer 112 can simply be printed at a conveniently located printing station. If the spacer layer 112 is applied by means of a tape cut from a sheet, it is required that the tape cut from the sheet be placed in the prescribed area of the sensor, so that the adhesive does not cover any area that must remain exposed. Likewise, if the spacer layer 112 is applied by means of printing of an adhesive, it is required that the adhesive be printed in the prescribed area of the sensor, so that the adhesive does not cover any area that must remain exposed.

The cover layer 116 is preferably made from an inert polymeric material. Representative examples of materials that can be used to form the cover layer 116 include, but are not limited to polyester, e.g., poly(ethylene terephthalate, polycarbonate, poly(vinyl chloride), etc. The dimensions of the cover layer 116 are not critical, but a typical cover layer 116 has a length of from about 15 mm to about 35 mm, a width of from about 3 mm to about 10 mm, and a thickness of from about 0.05 mm to about 1 mm.

Figure 7:
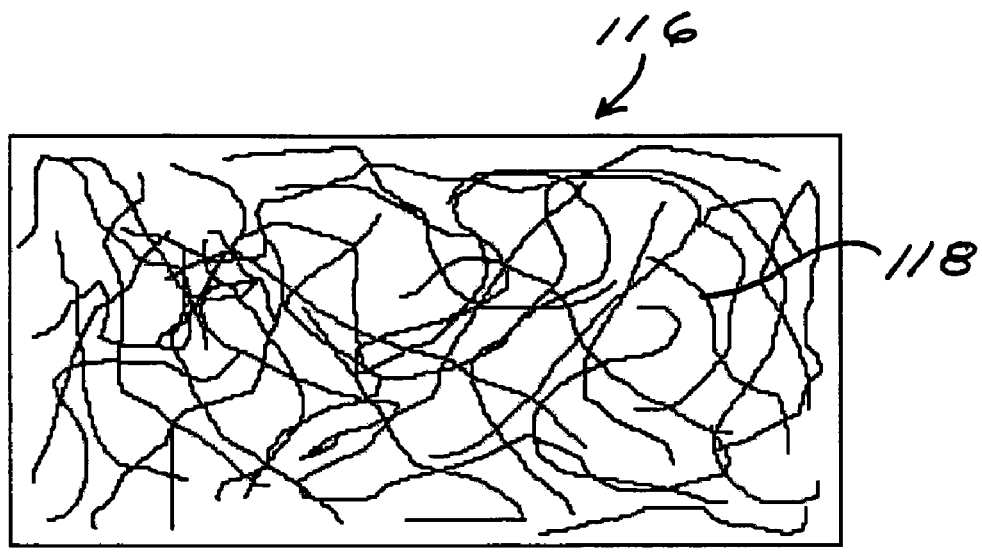
FIG. 7 is a plan view of one embodiment of the major surface of the cover layer that forms a wall of the flow channel. The embodiment employs a layer of non-woven mesh and a cover layer similar to that shown in FIG. 1.
Figure 8:
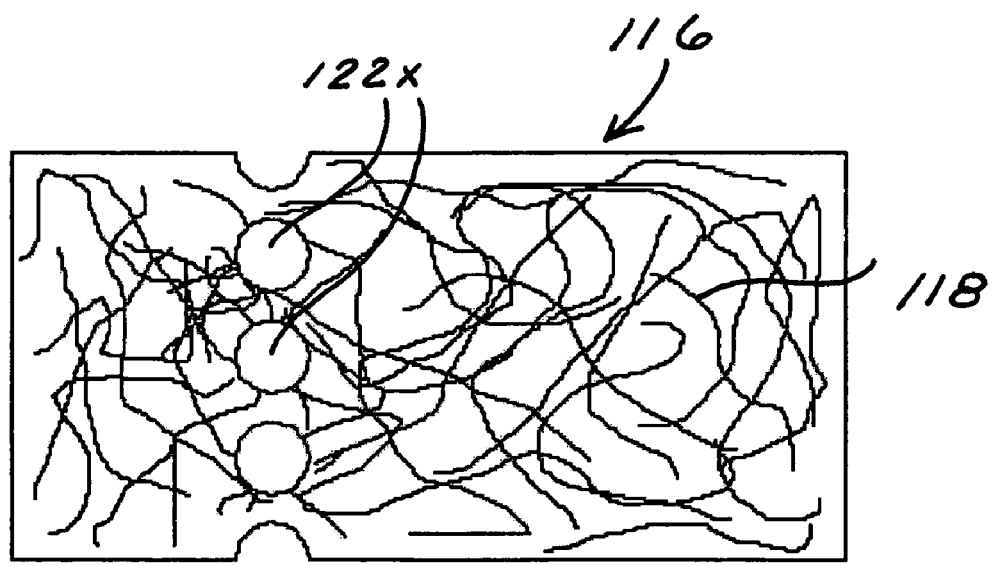
FIG. 8 is a plan view of another embodiment of the major surface of the cover layer that forms a wall of the flow channel. The embodiment employs a layer of non-woven mesh and a cover layer similar to that shown in FIG. 4.
Figure 9:
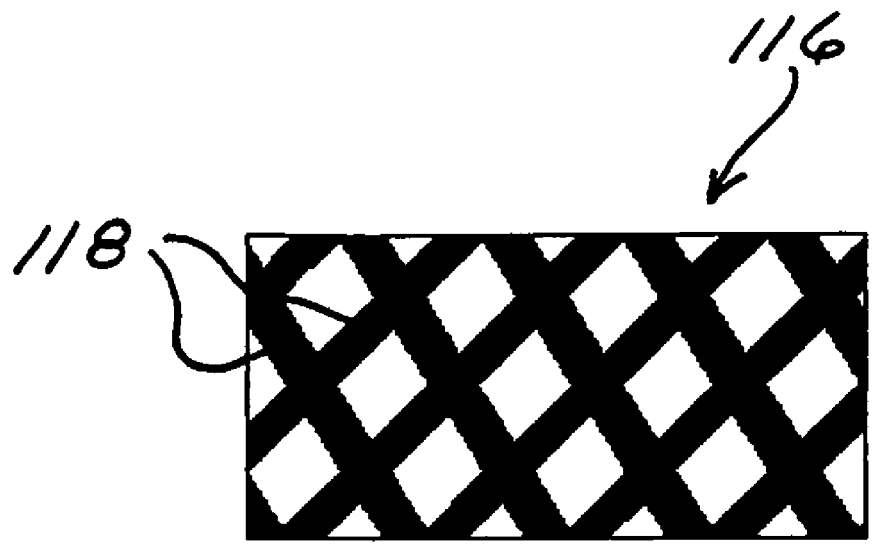
FIG. 9 is a plan view of still another embodiment of the major surface of the cover layer that forms a wall of the flow channel. The embodiment employs a layer of woven mesh and a cover layer similar to that shown in FIG. 1.
Figure 10:
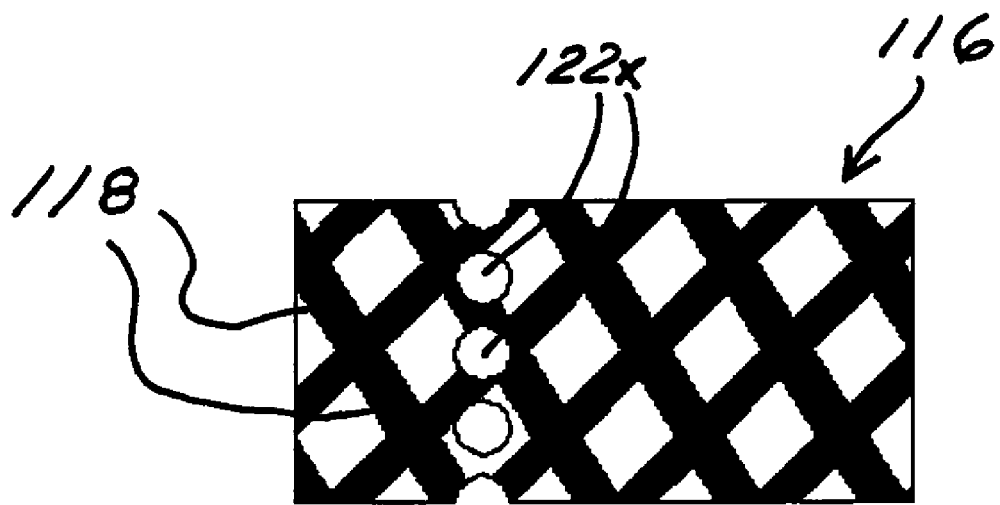
FIG. 10 is a plan view of still another embodiment of the major surface of the cover layer that forms a wall of the flow channel. The embodiment employs a layer of woven mesh and a cover layer similar to that shown in FIG. 4.
Figure 11:
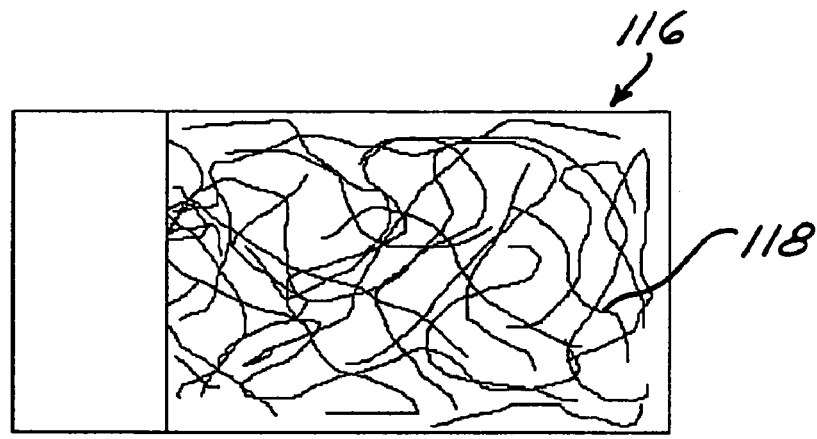
FIG. 11 is a plan view of still another embodiment of the major surface of the cover layer that forms a wall of the flow channel. A portion of the cover layer bears a layer of non-woven mesh. The cover layer is similar to that shown in FIG. 1.

The cover layer 116 has a layer of mesh 118 adhered thereto. The layer of mesh 118 can be formed from a woven or a non-woven mesh. A layer of mesh 118 is then deposited over the cover layer 116. The layer of mesh 118 can be laminated to the cover layer 116. The layer of mesh 118 can be impregnated with the reagents for the reaction of interest. Alternatively, the cover layer 116 can be printed with a pattern to simulate a layer of mesh (hereinafter referred to as a mesh-like pattern). The material thus printed can be soluble or insoluble in the sample medium. This printed mesh-like pattern may alternatively contain the reagents for the reaction of interest. FIGS. 7, 8, 9,10, and 11 illustrate various types of cover layers 116 having various types of layers of mesh bonded thereto. FIGS. 7, 9, and 11 show cover layers 116 of the type shown in FIGS. 1, 2, and 3. FIGS. 8 and 10 show cover layers 116 of the type shown in FIGS. 4, 5, and 6. FIGS. 7, 8, and 11 show layers of mesh 118 of the non-woven variety. FIGS. 9 and 10 show layers of mesh 118 of the woven variety. In FIG. 11, the layer of mesh 118 does not extend across the entire length of the cover layer 116. In FIGS. 7, 8, 9, and 10, the layer of mesh 118 extends across the entire length of the cover layer 116.

The cover layer 116 is preferably made of a polyester material (e.g., poly(ethylene terephthalate)) having a layer of mesh 118 laminated to a first major surface thereof. The mesh is preferably made of a polymeric material, e.g., polyester. Representative examples of materials suitable for use as a mesh-bearing cover layer 116 include Grade 3442 laminated mesh and Grade 3444 laminated mesh (Ahlstrom Paper Group, Mt. Holly Springs, Pa.). The laminated mesh comprises a spun-bonded polyester mesh laminated to a polyester film. It is preferred that the layer of mesh be made of a non-woven mesh. The thickness of the layer of mesh can range from about 5 µm to about 100 µm. Preferably the thickness of the layer of mesh ranges from about 25 µm to about 50 µm. The layer of mesh 118 does not contact the electrodes in the electrode arrangement.

Printing of a soluble mesh-like pattern on the surface of the cover layer 116 can be achieved by printing a cellulosic-based ink containing particulate materials, such as, for example, silica, carbon, titania, alumina, etc., or reagents, including, but not limited to, mediator, enzyme, buffers, etc., or both. Dimensions of the printed ink can range from about 5 µm to about 100 µm.

Printing of an insoluble mesh-like pattern on the surface of the cover layer 116 can be achieved by printing or spray coating a polymeric solution of preformed polymer or monomers that are polymerized after being applied. Dimensions of the printed ink can range from about 5 µm to about 100 µm.

The layer of mesh 118 can be coated with a surfactant. A surfactant coating is necessary only if the material of the layer of mesh 118 itself is hydrophobic (for example, nylon or polyester). If a hydrophilic layer of mesh is used, the surfactant coating can be omitted. The particular choice of surfactant is not critical, so long as it allows sufficiently uniform spreading of the sample. A preferred surfactant is "FC 170C FLUORAD" fluorochemical surfactant (3M, St. Paul, Minn.). "FLUORAD" surfactant is a solution of a fluoroaliphatic oxyethylene adduct, lower polyethylene glycols, 1,4-dioxane, and water. Another preferred surfactant is a silicone surfactant of the type described in U.S. Ser. No. 10/448,643, filed May 30, 2003, incorporated herein by reference. A surfactant loading of from about 15 to about 20 µg of surfactant/mg of mesh is preferred for most applications. The preferred surfactant loading will vary depending on the type of layer of mesh and surfactant used and the sample to be analyzed. The preferred surfactant loading can be determined empirically by observing flow of the sample through the layer of mesh 118 with different levels of surfactant.

An opening is required in the sensor strip to allow air to flow out of the flow channel 114. The opening can be placed in the base layer 102, the cover layer 116, or the spacer layer 112. In the preferred embodiment, at least one opening 122 is present in the cover layer 116 or base layer 102.

In an alternative embodiment, the cover layer 116 can have a plurality of openings 122x in the vicinity of the flow channel 114 to allow gases in the flow channel 114 to be removed upon the addition of the sample of fluid. See FIGS. 4, 5, 6, 8, and 10. The plurality of openings 122x allows reduction of the registration tolerance as compared to a system with a single opening in the cover layer 116. In other words, the openings 122x can be spaced apart in order to maintain the structural integrity of the sensor 100, with the result that some of the openings 122x may be positioned in such a way that they will not communicate with the flow channel 114, thereby preventing their ability to function as a vent. However, the formation of a plurality of openings 122x will result in providing venting and structural integrity of the sensor strip 100 formed in the spacer layer 112.

Figure 12:
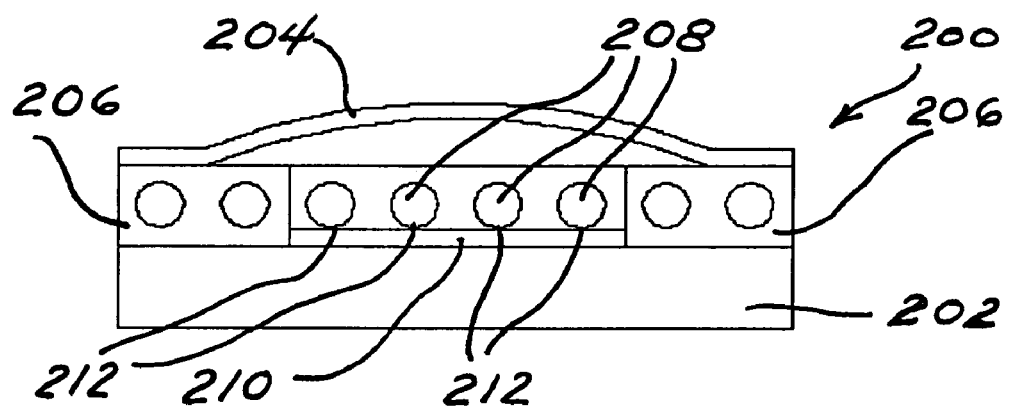
FIG. 12 is an end view of an electrode arrangement in a sensor of the prior art, wherein a layer of mesh is in contact with the surface of the electrodes in the electrode arrangement.

The invention described herein enhances the flow of the sample in flow channels where flow of sample would normally be inhibited. For example, viscous samples such as blood will fill narrow flow channels designed for low volume assays in a uniform manner. Confining contact of the layer of mesh to the cover layer and preventing the layer of mesh from contacting the electrodes in the electrode arrangement will increase the areas of the electrodes exposed to the sample, thereby enhancing the signal-to-noise ratio without affecting the sample's influence on the measurement. FIG. 12 shows a sensor 200 of the prior art having a base layer 202, a cover layer 204, and an insulating layer 206, in which fibers 208 of the mesh contact the electrodes 210 in the electrode arrangement, thereby preventing portions 212 of the electrodes 210 from contacting the sample. Only the fibers 208 running longitudinally are shown. Fibers running horizontally (not shown) would also contact the electrodes. Integration of the layer of mesh with the cover layer simplifies the process for manufacturing the sensor, thereby lowering the cost of the sensor.

The following non-limiting examples further illustrate this invention.

EXAMPLES

Example 1

This example illustrates the preparation of a sensor in the form of a strip according to this invention. The sensor strip of this example is shown in FIGS. 1, 2, and 3.

Carbon tracks are applied to a base layer made of poly (vinyl chloride) (PVC) by means of a screen-printing technique. The carbon tracks define the position of the electrodes within the reaction site, which includes the reference electrode, a dual-purpose counter/trigger electrode, and working electrode. The counter electrode also functions as a trigger electrode. The assay begins when the sample contacts the dual-purpose counter/trigger electrode. The carbon tracks also define the position of the contacts. A layer of electrically insulating material can be printed over carbon tracks, leaving the defined reaction site exposed. The layer of electrically insulating material is characterized by having a portion cut therefrom to create electrical contacts that can be inserted into a meter for measuring the reaction of interest. UV-curable adhesive can be printed to form the spacer layer and define the sidewalls of the flow channel. UV-curable adhesive is preferred to water-borne or solvent-borne adhesives, because the thickness of the cured layer is similar to the thickness of the uncured layer as applied. The cover layer comprises a polyester film laminated to a non-woven polyester mesh (Ahlstrom 3442) treated with surfactant.

In order for the sensor to be used, the sample enters the flow channel at the sample application zone located at the proximal end of the sensor and is caused to traverse the flow channel by wicking. Wicking is aided by the surfactant-treated mesh that is laminated to the cover layer. Flow of the sample is terminated when the sample reaches the air vent at the distal end of the sensor.

The proximal end of the sensor can optionally be trimmed to produce a sample application zone in which the sample is taken up at the proximal end of the sensor. This type of sensor is commonly referred to as an end-fill sensor. The invention is not limited to fabrication of a single end-fill sensor. A plurality of end-fill sensors can be fabricated at the same time. Following the fabrication of a plurality of end-fill sensors on a sheet, the sensors can be separated to create a plurality of individual sensors.

Example 2

In this example, the sensor of Example 1 is prepared, with the exception that a mixture of silver and silver chloride is printed on the track leading from the working electrode to reduce the resistance along that portion of the track.

Example 3

In this example, the sensor of Example 2 is prepared, with the exception that a reagent layer is printed on the working electrode. This optional reagent layer comprises an enzyme, a mediator, an optional binder, and an optional filler.

Example 4

In this example, the sensor of Example 3 is prepared, with the exception that a reagent layer is applied over all three electrodes.

Example 5

In this example, the sensor of Example 4 is prepared, with the exception that a layer comprising a mixture of silver and silver chloride is printed on the dual-purpose counter/trigger electrode and the reference electrode. This option is desired when the reagent layer cannot provide the reference voltage desired at the reference electrode.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A sensor strip comprising:
    (a) a base layer having a first major surface and a second major surface;
    (b) a cover layer having a first major surface and a second major surface, the first major surface of said cover layer facing the first major surface of said base layer, the first major surface of the cover layer having a layer of mesh adhered thereto;
    (c) a spacer layer interposed between the first major surface of said cover layer and the first major surface of said base layer to separate said cover layer from said base layer;
    (d) a flow channel having walls formed by said first major surface of said cover layer, said first major surface of said base layer, and said spacer layer, said flow channel having a reaction site therein, the layer of mesh not contacting the reaction site;
    (e) a sample application zone, where a liquid sample is introduced into said flow channel; and
    (f) at least one opening communicating with said flow channel to allow gas to be vented from said flow channel.

2. The sensor strip of claim 1, wherein said reaction site includes an electrode arrangement.

3. The sensor strip of claim 2, wherein said electrode arrangement comprises a working electrode and a dual-purpose reference electrode/counter electrode.

4. The sensor strip of claim 3, wherein said electrode arrangement further includes a trigger electrode.

5. The sensor strip of claim 3, wherein said electrode arrangement further includes a reagent system on at least said working electrode.

6. The sensor strip of claim 5, wherein said reagent system comprises an enzyme and a mediator for said enzyme.

7. The sensor strip of claim 2, wherein said electrode arrangement comprises a working electrode, a counter electrode, and a reference electrode.

8. The sensor strip of claim 7, wherein said electrode arrangement further includes a trigger electrode.

9. The sensor strip of claim 7, wherein said electrode arrangement further includes a reagent system on at least said working electrode.

10. The sensor strip of claim 9, wherein said reagent system comprises an enzyme and a mediator for said enzyme.

11. The sensor strip of claim 1, wherein said at least one opening is formed in said spacer layer.

12. The sensor strip of claim 1, wherein said at least one opening is formed in said cover layer.

13. The sensor strip of claim 1, wherein said spacer layer comprises a layer of adhesive.

14. The sensor strip of claim 1, wherein said spacer layer comprises a backing having a layer of adhesive on both major surfaces thereof.

15. A sensor strip comprising:
    (a) a base layer having a first major surface and a second major surface;
    (b) a cover layer having a first major surface and a second major surface, the first major surface of said cover layer facing the first major surface of said base layer, the first major surface of the cover layer having a layer of mesh adhered thereto;
    (c) a spacer layer interposed between the first major surface of said cover layer and the first major surface of said base layer to separate said cover layer from said base layer wherein said spacer layer comprises a layer of adhesive, wherein said adhesive is formed from a radiation-curable adhesive;
    (d) a flow channel having walls formed by said first major surface of said cover layer, said first major surface of said base layer, and said spacer layer, said flow channel having a reaction site therein, the layer of mesh not contacting the reaction site;
    (e) a sample application zone, where a liquid sample is introduced into said flow channel; and
    (f) at least one opening communicating with said flow channel to allow gas to be vented from said flow channel.

16. A sensor strip comprising:
    (a) a base layer having a first major surface and a second major surface;
    (b) a cover layer having a first major surface and a second major surface, the first major surface of said cover layer facing the first major surface of said base layer, the first major surface of the cover layer having a layer of mesh adhered thereto;

(c) a spacer layer interposed between the first major surface of said cover layer and the first major surface of said base layer to separate said cover layer from said base layer wherein said spacer layer comprises a layer of adhesive, wherein said adhesive is formed from a water-borne adhesive or a solvent-borne adhesive;

(d) a flow channel having walls formed by said first major surface of said cover layer, said first major surface of said base layer, and said spacer layer, said flow channel having a reaction site therein, the layer of mesh not contacting the reaction site;

(e) a sample application zone, where a liquid sample is introduced into said flow channel; and (f) at least one opening communicating with said flow channel to allow gas to be vented from said flow channel.

* * * * *